(12) United States Patent
Koslow et al.

(10) Patent No.: US 7,238,403 B2
(45) Date of Patent: *Jul. 3, 2007

(54) COMPOSITE FOR REMOVING MOISTURE, LIQUID AND ODORS WITH ANTI-MICROBIAL CAPABILITY

(75) Inventors: Evan E. Koslow, Weston, CT (US); Lawrence S. Walters, Jr., Woodbridge, CT (US)

(73) Assignee: KX Industries, LP, Orange, CT (US)

( * ) Notice: Subject to any disclaimer, the term of this patent is extended or adjusted under 35 U.S.C. 154(b) by 61 days.

This patent is subject to a terminal disclaimer.

(21) Appl. No.: 10/322,271

(22) Filed: Dec. 18, 2002

(65) Prior Publication Data

US 2003/0087086 A1 May 8, 2003

Related U.S. Application Data

(60) Continuation-in-part of application No. 10/238,431, filed on Sep. 9, 2002, now abandoned, which is a division of application No. 09/579,205, filed on May 26, 2000, now Pat. No. 6,485,813, which is a continuation-in-part of application No. 08/903,395, filed on Jul. 22, 1997, now Pat. No. 6,077,588, which is a division of application No. 08/813,055, filed on Mar. 7, 1997, now Pat. No. 5,792,513.

(51) Int. Cl.
*B32B 5/02* (2006.01)
*B32B 5/16* (2006.01)
*B32B 7/12* (2006.01)

(52) U.S. Cl. .......................... 428/76; 428/74; 428/114; 604/358; 604/368; 604/370; 156/283

(58) Field of Classification Search ................ 156/283; 428/74, 114; 604/358, 370
See application file for complete search history.

(56) References Cited

U.S. PATENT DOCUMENTS

| | | | | | |
|---|---|---|---|---|---|
| 4,668,566 | A | * | 5/1987 | Braun | 442/118 |
| 4,857,065 | A | * | 8/1989 | Seal | 604/368 |
| 4,900,377 | A | * | 2/1990 | Redford et al. | 156/62.2 |
| H1732 | H | * | 6/1998 | Johnson | 428/68 |
| 5,843,267 | A | * | 12/1998 | Cashaw et al. | 156/324 |
| 5,944,706 | A | * | 8/1999 | Palumbo et al. | 604/368 |
| 6,077,588 | A | * | 6/2000 | Koslow et al. | 428/114 |
| 6,162,962 | A | * | 12/2000 | Hinsch et al. | 623/11.11 |

FOREIGN PATENT DOCUMENTS

EP 631768 A1 * 1/1995

* cited by examiner

*Primary Examiner*—Sam Chuan Yao
(74) *Attorney, Agent, or Firm*—DeLio & Peterson, LLC

(57) ABSTRACT

There is provided a composite comprising a bonded mixture of a binder and active ingredients such as spill control agents, odor control agents, anti-microbial agents, and biologically active agents. The mixture is applied to and fused and/or coalesced with a first substrate, preferably an nonwoven material that is fluid permeable or impermeable. The composite preferably contains a second substrate, preferably a nonwoven material, placed on top of the mixture that is fused to and/or coalesced with the mixture. Preferably, the composite adsorbs and/or absorbs moisture, liquids, and/or odors, and can provide an anti-microbial effect. The composite can be used to line an outer or inner functional surface such as a shelf, a drawer, a cabinet, a refrigerator, trash receptacle, shipping container, or as a backing for other surfaces such as carpeting, fabric, upholstery, drapes, and the like.

16 Claims, 3 Drawing Sheets

COMPOSITE FOR REMOVING MOISTURE, LIQUID AND ODORS WITH ANTI-MICROBIAL CAPABILITY

This is a continuation-in-part of U.S. patent application Ser. No. 10/238,431, filed on Sep. 9, 2002, which is a divisional application of U.S. patent application Ser. No. 09/579,205, filed May 26, 2000, now U.S. Pat. No. 6,485,813, which is a continuation-in-part of U.S. patent application Ser. No. 08/903,395, filed on Jul. 22, 1997, now U.S. Pat. No. 6,077,588, which is a divisional application of U.S. patent application Ser. No. 08/813,055, filed on Mar. 7, 1997, now U.S. Pat. No. 5,792,513.

This invention relates generally to a composite that has the ability to absorb or adsorb moisture, liquids and/or odors, control microorganisms such as viruses, bacteria, and molds, or combinations thereof.

There is a need for lining or cushioning the underside of decorative substrates such as carpets, rugs, upholstery and drapes, or the interior surfaces of enclosed areas such as cabinets, drawers or appliances, with a material that absorbs or adsorbs moisture, liquids, as well as odors, to prevent damage to the decorative substrates or interior surfaces from various types of assault. Relevant types of assault include food and drink spills, food spoilage, water leaks, tobacco smoke, heavy foot traffic, animal wastes, and cleaning chemicals.

Lining or cushioning materials can be used under substrates or placed over surfaces. Likewise, placing these types of linings or cushioning materials on shelves, drawers, and cabinets also can serve aesthetic, hygienic, and/or safety purposes.

Prior art lining and cushioning materials that do not adequately absorb or adsorb either moisture, liquids or odors leave surfaces subject to mildew and other types of destruction that include microorganism assault.

SUMMARY OF THE INVENTION

The present invention is directed to a composite comprising a fluid impermeable substrate; and a bonded mixture coalesced on a surface of the fluid impermeable substrate, the bonded mixture comprising binder, and active ingredients comprising a spill control agent, an odor control agent, or combinations thereof. Preferably, the composite further includes a second substrate opposite the bonded mixture. The composite can further include an anti-microbial agent.

In another aspect, the present invention is directed to a composite useful for odor control comprising a liquid permeable substrate; a liquid impermeable substrate; and a bonded mixture, in between the liquid permeable substrate and the liquid impermeable substrate, comprising a spill control agent, an odor control agent, an anti-microbial agent, or combinations thereof.

In yet another aspect, the present invention is directed to a composite liner for use with a container, drawer or shelf to absorb spills of liquids and for odor control within the container, drawer or shelf, the composite liner comprising a liquid impervious backing layer; and an odor controlling liquid absorbent layer comprising a stabilized matrix of thermoplastic fibers, an absorbent material and an odor controlling material.

In still yet another aspect, the present invention is directed to a process of controlling odor and spills in an enclosed compartment or shelf comprising providing a liner within the enclosed compartment or on the shelf, the liner comprising a fluid permeable substrate; a fluid impermeable substrate; and a bonded mixture, in between the fluid permeable substrate and the fluid impermeable substrate, comprising a spill control agent and an odor control agent.

The first or second substrate can be a floor covering, carpeting, a rug, a mat, upholstery, a curtain, a drape, a slip cover, a shelf liner, fabric, wall covering, a pad, and the like. Preferably, the composite is attached to or placed in or on a drawer, a shelf, a cabinet interior, trash receptacle, shipping container, or a refrigerator compartment, or any surface that requires odor and/or spill control, and/or microbial control.

DETAILED DESCRIPTION OF THE INVENTION

The present invention provides for a composite that can absorb and/or adsorb moisture, liquids, and/or odors, provide an anti-microbial effect, or combinations thereof. The composite comprises a first substrate having a mixture of one or more active ingredients and a binder that are bonded to each other and to the first substrate. The active ingredients of the composite can be any suitable particle selected to perform a suitable function including, but are not limited to, spill control agents such as adsorbent materials, and/or absorbent materials, materials that can release liquid or gas held therein, biologically active agents, and the like. The binder is preferably, on average, smaller than the active ingredient, and at least some of the binder coalesces at least some of the active ingredients to each other, and to the first substrate.

Also, the present invention provides for the above composite having a second substrate located such that the mixture of active ingredients and binder is between the first substrate and the second substrate, wherein at least some of the active ingredients are coalesced by the binder to each other, to the first substrate, and/or to the second substrate. Either or both the first substrate and second substrate may be a decorative substrate having an aesthetically pleasing design, composition, structure or appearance.

The present invention further provides for a method of producing the above composite having the steps of applying a mixture of binder and one or more active ingredients to one or more substrates, applying heat to the mixture on the one or more substrates, and applying pressure to the mixture and the one or more substrates such that the binder coalesces the one or more active ingredients to themselves, and to the one or more substrates.

The thin, flexible composite of the present invention that can be used to line an outer or inner functional surface such as a shelf, a drawer, a cabinet, a refrigerator, trash receptacle, shipping container, or can be used as a functional backing for other porous products such as carpeting, rugs, upholstery, drapes, and the like. The thin, flexible composite having odor control and spill control capabilities, and preferably, anti-microbial capabilities, is well suited for placement inside an enclosed area such as a cabinet, drawer, container, or appliance where odor and liquid adsorption/absorption are needed to provide a sanitary environment.

Figure 1:
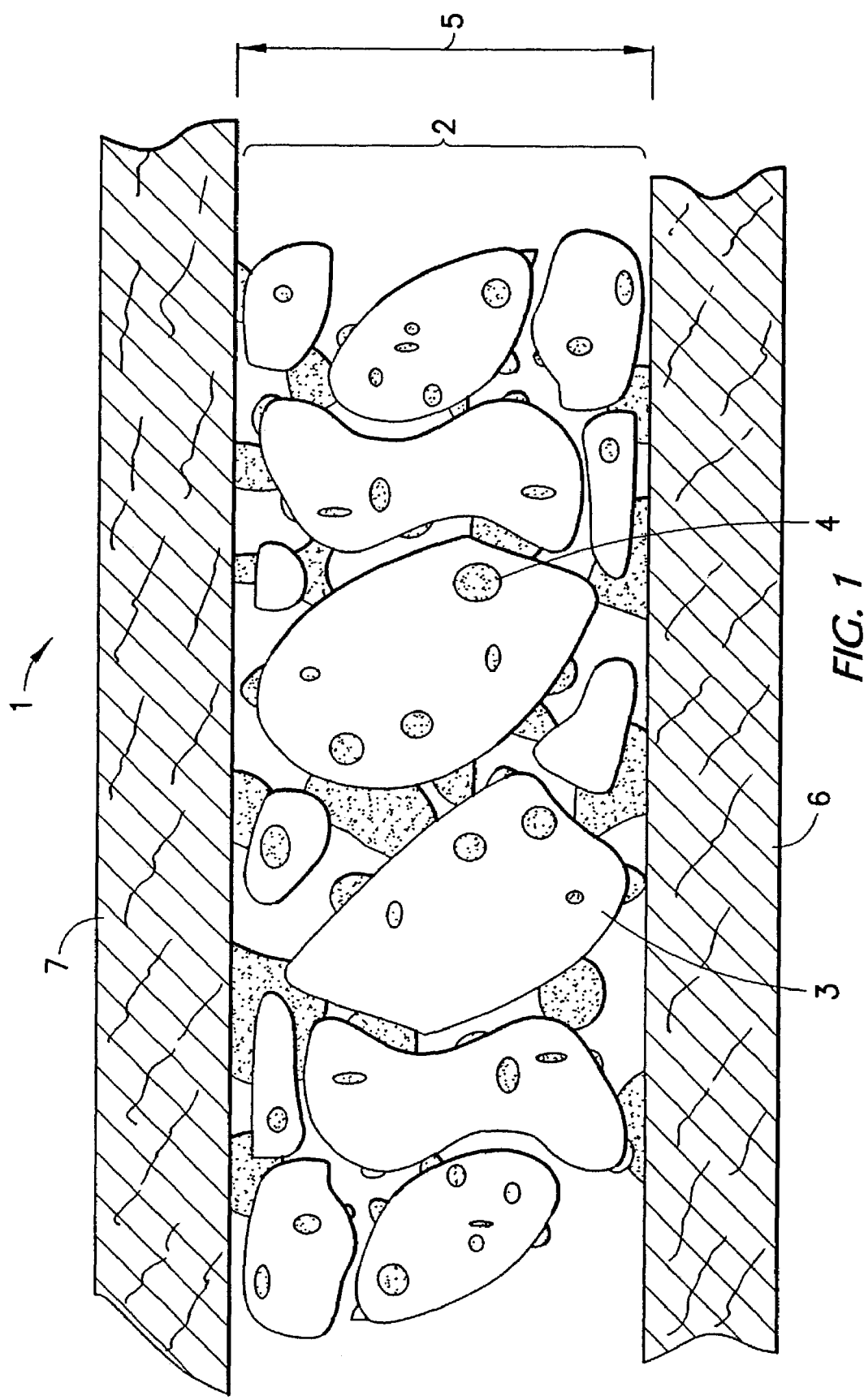
FIG. 1 is a cross-sectional view of a preferred embodiment of the composite of the present invention.

Referring to the drawings, and in particular FIG. 1, there is provided a composite generally indicated as 1. The composite 1 has a first substrate 6 and, optionally, a second substrate sometimes referred to as a backing or covering layer 7. First substrate 6 and second substrate 7 can be formed of various materials depending upon the intended application and need not be formed of the same or similar material within one composite.

First substrate 6 can be a permeable or semi-permeable woven, nonwoven or partially woven sheet of fibrous or semi-fibrous materials, or a membrane. The material can be, for example, rayon, polyester, nylon, polypropylene, polyethylene, cotton, wood pulp, natural fibers, PTFE, organic fluoropolymers, or a combination thereof. First substrate 6 can optionally be formed using cellulosic materials, such as tissue or towel-stock, or a combination of cellulosic and thermoplastic, synthetic, or natural fibers. First substrate 6 can also be an impermeable material, such as a metal foil, plastic sheet or film (e.g., MYLAR®, TEFLON®, nylon), a semi-permeable sheet or membrane, an adhesive coated sheet or film, a non-adhesive fastener i.e., VELCRO®, or a combination thereof.

First substrate 6 can be formed from any suitable material, by any suitable process known in the art. Examples of such processes include, but are not limited to, and by way of illustration only, meltblowing, spunbonding, carding, wet or dry laid processes, islands-in-sea, and air laying. In addition, the substrate material can be used alone, or in combination with any suitable substrate binder including, for example, lignin, starch, acrylic, vinyl acrylic, styrene-butadiene, and the like.

By way of example only, first substrate 6 can be used as a backing for floor coverings, carpeting, rugs, mats, upholstery, curtains, drapes, slipcovers, shelf liners, fabric, wall coverings, and the like. First substrate 6 can be selected to provide a notable level of system activity, however, it need not be capable of providing system activity as an essential or non-essential function. First substrate 6 can be a decorative substrate with an aesthetically pleasing design, composition, structure or appearance.

Second substrate 7 can be the same or different material as first substrate 6.

Coalesced with first substrate 6, and optionally with second substrate 7, is mixture 2. Mixture 2 has one or more active ingredients 3 and binder 4. The binder 4 coalesces at least some of the active ingredients 3 into a bonded mixture. An amount of binder 4 also coalesces at least some of active ingredients 3 to first substrate 6, and optionally to second substrate 7, or to both substrates 6 and 7.

Suitable active ingredients 3 include any material that performs a suitable function including, but not limited to, spill control agents such as absorbents and/or adsorbents, biologically active materials, anti-microbial agents, odor control agents, and the like. Furthermore, active ingredients 3 can be coated with and/or impregnated with a suitable active ingredient that can be released. Such an active ingredient includes, but is not limited to, lubricants, herbicides, pesticides, insecticides, fungicides, fragrances, humectants, desiccants, anti-microbial agents, malodor absorbing agents, biologically active agents, dyes, indicators, or a combination thereof.

Exemplary of suitable active ingredients 3 include, but are not limited to: iodinated resin, activated carbon, activated alumina, metal powders including those with magnetic properties, alumina-silicates, super absorbent polymers, metal oxides, zeolites, glass beads, ceramics, diatomaceous earth, macroporous polymers, aerogels, cellulosic materials, anti-microbial agents, fragrances, fragrant materials, glass, titanates, starches, foamed polymer absorbents, macroporous super absorbent polymers, perlite, carbon, anion exchange media, cationic exchange media, protein solids, organic acids and salts thereof, inorganic acids and salts thereof, minerals, acrylic based polymers, clay, metal oxihydrates, talcum, sodium bicarbonate, silicic acid, metal hydroxides, modified cellulose, cellulose, dyes, indicators, liquid absorbing compounds, malodor absorbing agents, molecular sieves, phosphates, biologically active agents, or a combination thereof.

Active ingredients 3 have an average particle size from about 5 microns to about 5000 microns, preferably from about 100 microns to about 1000 microns.

Binders useful in the present invention for coalescing active ingredients 3 can potentially include any thermoplastic or thermoset material known in the art in either fiber, powder or particulate form. Useful binder particles 4 can include materials such as, but not limited to, polyolefins, polyvinyl halides, polyvinyl esters, polyvinyl ethers, polyvinyl sulfates, polyvinyl phosphates, polyvinyl amines, polyamides, polyimides, polyoxidiazoles, polytriazols, polycarbodiimides, polysulfones, polycarbonates, polyethers, polyarylene oxides, polyesters, polyarylates, phenol-formaldehyde resins, melamine-formaldehyde resins, formaldehyde-ureas, ethyl-vinyl acetate copolymers, co-polymers and block interpolymers thereof, and combinations thereof. Variations of the above materials and other useful polymers include the substitution of groups such as hydroxyl, halogen, lower alkyl groups, lower alkoxy groups, monocyclic aryl groups, and the like.

Useful thermoplastic binders 4 include, by way of illustration only, polyalkylenes, polyethers, polyvinyl esters, polyvinyl ethers, ethylene-vinyl acetate copolymers, end-capped polyacetals, such as poly(oxymethylene) or polyformaldehyde, poly(trichloroacetaldehyde), poly(n-valeraldehyde), poly(acetaldehyde), poly(propionaldehyde), and the like; acrylic polymers, such as polyacrylamide, poly(acrylic acid), poly(methacrylic acid), poly(ethyl acrylate), poly(methyl methacrylate), and the like; fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), poly(vinyl fluoride), and the like; polyamides, such as poly(6-aminocaproic acid) or poly(ε-caprolactam), poly(hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly-(sulfonyl-1,4-phenyleneoxy-1,4-phenylenesulfonyl-4,4'-biphenylene), and the like; polycarbonates, such as poly(bisphenol A) or poly(carbonyldioxy-1,4-phenyleneisopropylidene-1,4-phenylene), and the like; polyesters, such as poly(ethylene terephthalate), poly(tetramethylene terephthalate), poly(cyclohexylene-1,4-dimethylene terephthalate) or poly(oxymethylene-1,4-cyclohexylenemethyleneoxyterephthaloyl), and the like; polyaryl sulfides, such as poly(p-phenylene sulfide) or poly(thio-1,4-phenylene), and the like; polyimides, such as poly(pyromellitimido-1,4-phenylene), and the like; polyolefins, such as polyethylene, polypropylene, poly(1-butene), poly (2-butene), poly(1-pentene), poly(2-pentene), poly(3-methyl-1-pentene), poly(4-methyl-1-pentene), and the like; vinyl polymers, such as poly(vinyl acetate), poly(vinylidene chloride), poly(vinyl chloride), and the like; diene polymers, such as 1,2-poly-1,3-butadiene, 1,4-poly-1,3-butadiene, polyisoprene, polychloroprene, and the like; polystyrenes; copolymers of the foregoing, such as acrylonitrile-butadiene-styrene (ABS) copolymers, and the like, or a mixture thereof.

In addition, suitable binders 4 can be produced from thermoset resins, which include phenol-formaldehyde or melamine resins, with or without additional crosslinking agents, epoxies, such as the diglycidylether from epichlorohydrin and bisphenol A, phenolics, alkyds, amino resins, polyurethanes, phenolfurfurals, cellulose acetates, cellulose nitrates, bisamylamide and the like, or a combination thereof.

Preferred binders 4 are polyethylene, polypropylene, poly(ethylene vinyl acetate), nylon, or combinations thereof.

Preferably, binder 4 is present in such an amount and at such a size that it does not substantively interfere with the functioning of active ingredients 3. Binder 4 preferably has an average particle size or diameter size of about 5 microns to about 100 microns. In addition, binder 4 is generally significantly smaller in average size than active ingredients 3. More preferably, binder 4 when in particulate form is about 4 to 25 times smaller, on average, than the average size of active ingredients 3.

Figure 2:
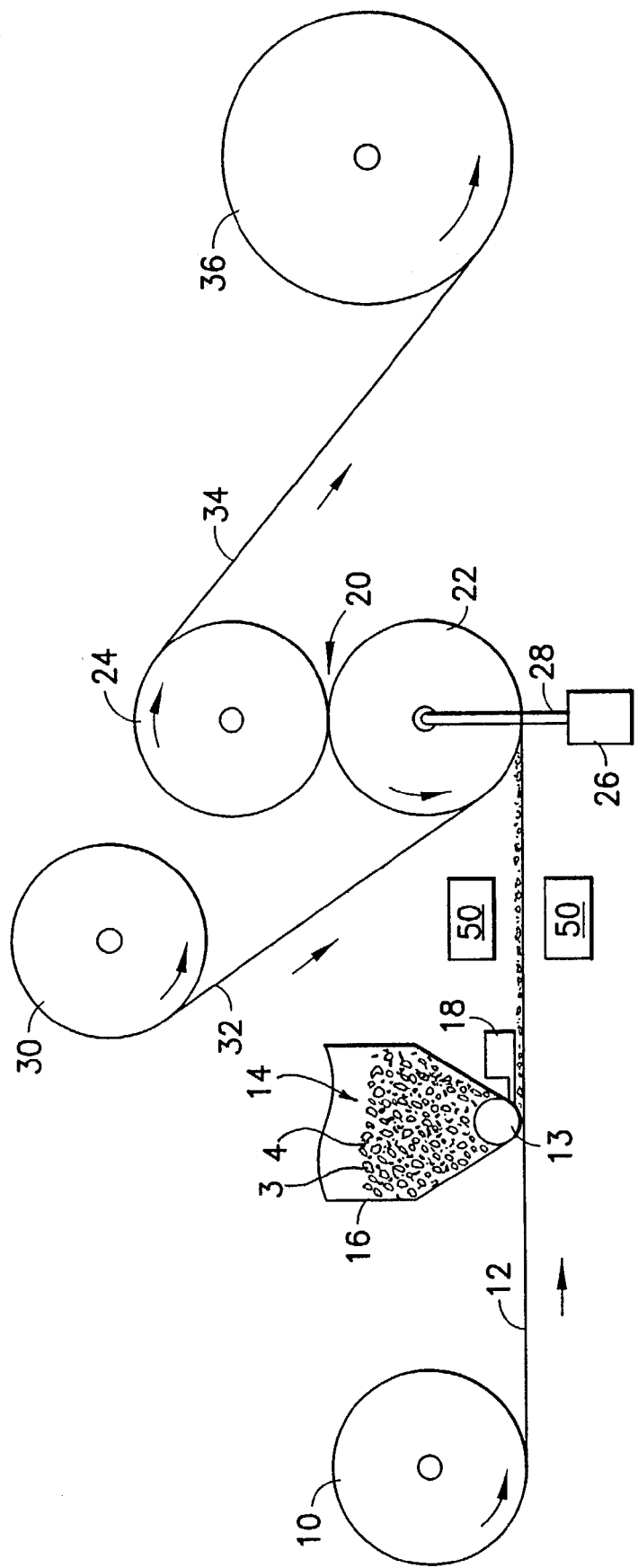
FIG. 2 is a schematic diagram illustrating an apparatus and process for making the composite of the present invention.

FIG. 2 illustrates an exemplary apparatus used to produce this invention. A supply roll 10 provides first substrate 12. Downstream from supply roll 10 is a knurled roller 13 positioned to receive a mixture of active ingredients 3 and binder particles 4, generally indicated as mixture 14, from hopper 16. Mixture 14 is applied to the upper surface of substrate 12 as a continuous coating or, alternatively, as a coating in a specific design including, but not limited to, stripes. A brush 18 can be employed to aid in removing mixture 14 from knurled roller 13.

Thereafter, substrate 12 containing mixture 14 is passed through nip 20 between a heated idler roller 22 and a drive roller 24. Alternatively, before being passed through nip 20, substrate 12 containing mixture 14, can be preheated by a pre-heater 50 such as, for example, a convection or infrared oven. A pneumatic cylinder 26 is connected via a rod 28 to the axle of idler roller 22 to maintain a desired pressure on substrate 12 containing mixture 14 within nip 20. Alternatively, drive roller 24 may be heated as well while the axle of idler roller 22 can also be attached to a pneumatic cylinder, not shown, to maintain pressure on substrate 12. In passing through pre-heater 50, and over the surface of heated roller 22, mixture 14 is heated to a temperature equal to or greater than the softening temperature of binder particles 4, but not to a temperature above the softening temperature of active ingredients 3. Within nip 20, binder 4 coalesce under heat and pressure with active ingredients 3. An amount of binder 4 coalesces with first substrate 12.

Furthermore, in a preferred embodiment of the present invention, a second supply roll 30 of a second substrate 32, is also passed between nip 20 on the top of mixture 14. An amount of binder 4 coalesces with second substrate 32. Upon leaving nip 20, binder 4 cools and hardens. The finished composite 34 then passes onto take-up roll 36.

By selecting substrate materials 12 and 32, binder 4, active ingredients 3, active ingredients to binder weight ratios, absolute amounts of mixture 14 applied to substrate 12 per unit area, binder size, active ingredient size, the ratio of binder size to active ingredient size, heating temperature, nip pressure and the linear speed of first substrate 12, it is possible to vary composite depth, porosity, permeability, tensile strength, flexibility, pleatability, draping ability, and other attributes of the composite of the present invention.

Figure 3:
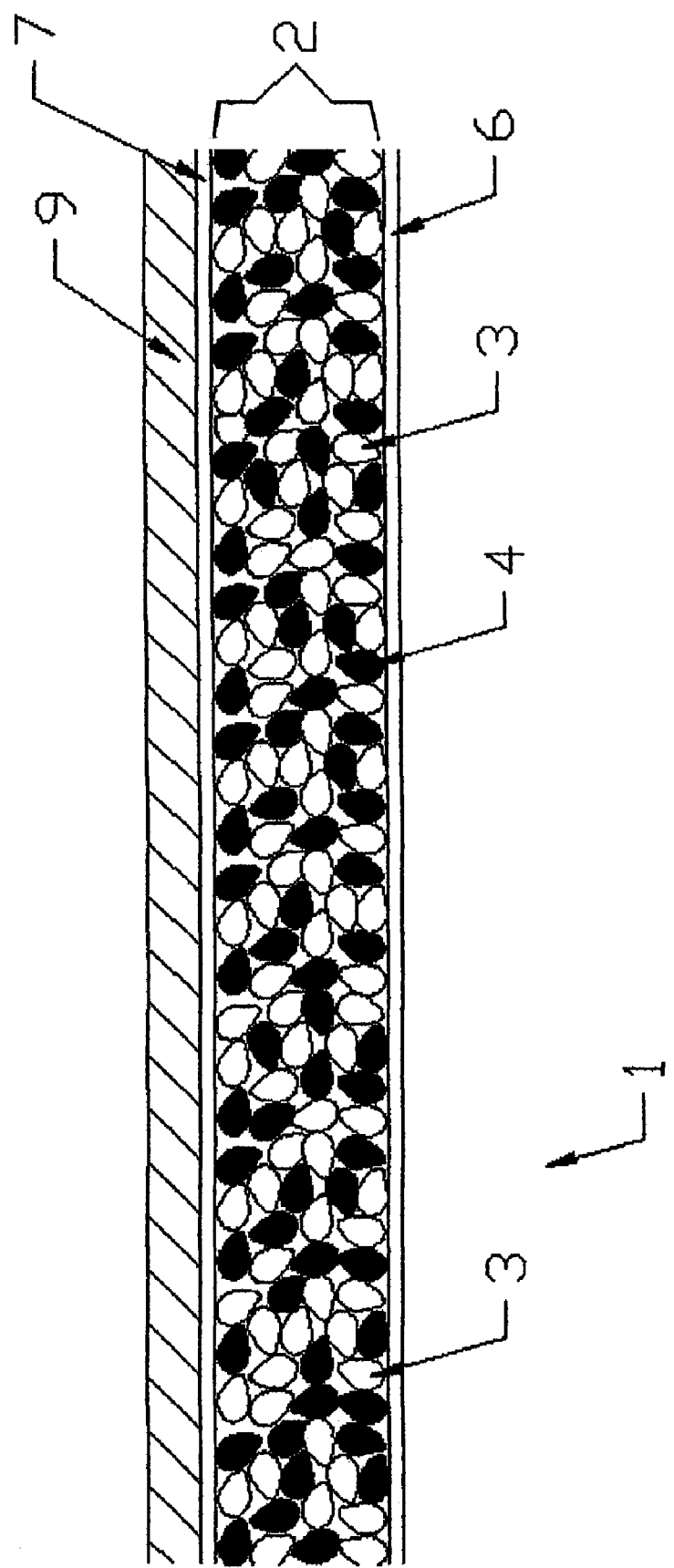
FIG. 3 is a cross-sectional view of a composite of the present invention in contact with a surface.

As shown in FIG. 3, composite 1 can be used on, under, on the side of, and/or attached to any suitable surface 9, which include, for example, a shelf, a drawer, a cabinet, and/or an inside surface of a refrigerator or compartment thereof. Preferably, composite 1 is physically attached to surface 9. Optionally, composite 1 can be at least partially attached to, or combined with any suitable surface 9 by any suitable method. For example, composite 1 can be fused, glued, tacked, stapled, chemically adhered, mechanically adhered, hooked, sewn, or otherwise joined with suitable surface 9. Alternatively, composite 1 can be placed in direct proximity with suitable surface 9 without a bond or mechanical fastener. When the active ingredients include metal powders with magnetic properties, composite 1 can adhere to a metal surface containing iron or steel through magnetic induction.

Another feature of composite 1 is that the thermoplastic and/or thermoset binder preferably imparts a measure of flowability. For example, small holes made in composite 1 by a needle or a tack will generally seal themselves once the needle or tack is removed from composite 1. Thus, composite 1 is preferably resilient and self-healing.

Although the present invention has been described with respect to one or more particular embodiments, it will be understood that other embodiments of the present invention can be employed without departing from the spirit and scope of the present invention. Hence, the present invention is deemed limited only by the appended claims and the reasonable interpretation thereof.

What is claimed is:

1. A composite comprising:
   a liquid permeable substrate;
   a bonded mixture comprising binder and active ingredients; and
   a liquid impermeable substrate located such that said bonded mixture is between said liquid permeable substrate and said liquid impermeable substrate, wherein at least some of said active ingredients are coalesced by said binder to each other, to said liquid permeable substrate, and to said liquid impermeable substrate and wherein said binder is significantly smaller in average size than said active ingredients.

2. The composite of claim 1 further including an antimicrobial agent.

3. The composite of claim 1 wherein the active ingredients have activity properties selected from the group consisting of liquid absorption, odor adsorption and medicament delivery.

4. The composite of claim 3 wherein the active ingredients comprise a liquid absorption agent selected from the group consisting of super absorbent polymers, fibrous materials, polymers, silica, zeolites, diatomaceous earth, glass, activated bauxite, and aluminum silicates.

5. The composite of claim 3 wherein the active ingredients comprise an odor control agent for odor absorption selected from the group consisting of sodium bicarbonate, activated carbon, zeolites, ion exchange media, activated alumina, and silicates.

6. The composite of claim 1 wherein the binder is selected from the group consisting of: a thermoplastic binder, and a thermoset binder.

7. A composite comprising:
a fluid permeable substrate;
a fluid impermeable substrate; and
a bonded mixture comprising a binder and active ingredients, said bonded mixture is between said fluid impermeable substrate and said fluid permeable substrate, wherein at least some of said active ingredients are coalesced by said binder to each other, to said fluid impermeable substrate, and to said fluid permeable substrate, wherein said binder is significantly smaller in average size than said active ingredients.

8. The composite of claim 7 wherein said active ingredients have activity properties selected from the group consisting of liquid absorption, odor adsorption and medicament delivery.

9. The composite of claim 8 wherein the active ingredients comprise a liquid absorption agent selected from the group consisting of a fibrous mat, and an absorbent.

10. The composite of claim 8 wherein the active ingredients comprise an odor control agent for odor absorption selected from the group consisting of sodium bicarbonate, activated carbon, zeolites, ion exchange media, activated alumina, and silicates.

11. The composite of claim 7 further including a fragrance or a fragrance releasing agent.

12. A composite comprising:
a permeable substrate;
an impermeable substrate; and
a mixture layer comprising a stabilized matrix of a binder and active ingredients, wherein at least some of said active ingredients are coalesced by said binder to each other, to said permeable substrate, and to said impermeable substrate, and wherein said binder is significantly smaller in average size than said active ingredients and present in an amount that does not substantively interfere with functioning of said active ingredients.

13. The composite of claim 12 wherein said active ingredients absorb or adsorb liquids or gases.

14. The composite of claim 12 wherein said binder has an average diameter about 4 to 25 times smaller than the average size of the active ingredients.

15. The composite of claim 12 wherein said active ingredients have a size in the range of about 5 microns to about 5000 microns.

16. The composite of claim 15 wherein said binder has an average diameter size of about 5 microns to about 100 microns.

* * * * *